United States Patent [19]

Parker et al.

[11] Patent Number: 5,653,960
[45] Date of Patent: Aug. 5, 1997

[54] TETRA-AZA MACROCYCLES, PROCESSES FOR THEIR PREPARATION AND THEIR USE IN MAGNETIC RESONANCE IMAGING

[75] Inventors: David Parker, Durham; Nigel Robert Arnold Beeley, Thame, both of United Kingdom

[73] Assignee: Celltech Therapeutics Limited, Slough, United Kingdom

[21] Appl. No.: 311,721

[22] Filed: Sep. 23, 1994

Related U.S. Application Data

[63] Continuation of Ser. No. 175,489, Dec. 29, 1993, abandoned, Continuation of Ser. No. 41,299, Mar. 29, 1993, abandoned, which is a continuation of Ser. No. 793,374, filed as PCT/GB91/00605, Apr. 18, 1991 published as WO91/16081, Oct. 31, 1991, abandoned.

[30] Foreign Application Priority Data

| Apr. 18, 1990 | [GB] | United Kingdom | 9008720 |
| Apr. 18, 1990 | [GB] | United Kingdom | 9008724 |
| Aug. 3, 1990 | [GB] | United Kingdom | 9017148 |
| Mar. 1, 1991 | [GB] | United Kingdom | 9104391 |

[51] Int. Cl.[6] .............. A61B 5/055; A61K 49/00; C07D 255/02; C07D 255/00
[52] U.S. Cl. .............. 424/9.363; 514/79; 514/836; 534/15; 534/16; 540/465; 540/474
[58] Field of Search .............. 424/9, 9.363; 540/465, 540/474; 514/79, 836; 534/15, 16

[56] References Cited

U.S. PATENT DOCUMENTS

| 4,174,319 | 11/1979 | Kobuke | 260/239 |
| 4,174,428 | 11/1979 | Tabushik et al. | 540/474 |
| 4,432,907 | 2/1984 | Wieder et al. | 436/500 |
| 4,472,509 | 9/1984 | Gansow et al. | 436/548 |
| 4,659,839 | 4/1987 | Nicolotti et al. | 548/546 |
| 4,671,958 | 6/1987 | Rodwell et al. | 514/2 |
| 4,678,667 | 7/1987 | Meares | 424/85 |
| 4,702,998 | 10/1987 | Tanaka et al. | 540/454 |
| 4,877,600 | 10/1989 | Bonnemain et al. | 257/2 |
| 4,885,363 | 12/1989 | Tweedle et al. | 540/465 |
| 5,049,667 | 9/1991 | Schaefer et al. | 540/474 |
| 5,053,503 | 10/1991 | Dean et al. | 540/474 |
| 5,342,606 | 8/1994 | Sherry et al. | 424/9 |

FOREIGN PATENT DOCUMENTS

| 76217/87 | 2/1988 | Australia. | |
| 0173629 | 8/1985 | European Pat. Off. | |
| 0188256 | 7/1986 | European Pat. Off. | |
| 0232751 | 8/1987 | European Pat. Off. | 540/474 |
| 0255471 | 2/1988 | European Pat. Off. | |
| A 0372582 | 8/1990 | European Pat. Off. | |
| 0382582 | 8/1990 | European Pat. Off. | |
| 0455380 | 11/1991 | European Pat. Off. | |
| 1098937 | 3/1983 | U.S.S.R. | |
| 88/08422 | 11/1988 | WIPO. | |
| 89/01476 | 2/1989 | WIPO. | |

OTHER PUBLICATIONS

Broan et al., "Synthesis and Complexation Behaviour of an Effective Octadentate Complexone 1,4,7,10–Tetraazacyclododecane–1,4,7,10–tetrakis[methylene(methylphosphinic acid)]", *J. Chem. Soc., Chem. Commun.*, pp. 1739–1741 (1st Dec. 1990).

Kabachnik et al., "Synthesis and Acid–Base and Complex–Forming Properties of 1,4,7,10–tetrakis(dihydroxyphosphorylmethyl)–1,4,7,10–tetraazacyclododecane", *Bull. Acad. Sci. USSR*, 33(4), pp. 777–782 (1984).

Khaw et al., *Science*, 209, 295 (1980).

Krejcarek et al., *Biochem. Biophys. Res. Comm.*, 77, 581 (1977).

Childs, R.L. and Hnatowich, D.J., *J. Nuc. Med.* 26, 293 (1985).

Stetter, H., et al., *Angew. Chem. Int. Ed. Engl.*, 15, 686 (1976).

Loncin, J.F., et al., *Inorg. Chem.*, 25, 2646 (1986).

Moi, C.F., et al., *J. Am. Chem. Soc.*, 110 6266 (1988).

Tweedle, M.F., et al., *J. Nuc. Med.*, 28, 705 (1988).

Goodwin, C.H., et a., *J. Nuc. Med.*, 27, 959 (1986).

Paik, C.H., et al., *J. Nuc. Med.*, 28, 572 (1987).

Paik, C.H., et al., *J. Nuc. Med.*, 29, 889 (1988).

Haseman, C.F., et al., *Eur. J. Nuc. Med.*, 12, 455 (1986).

Parker et al., *Pure & Appl. Chem.*, vol. 61, No. 9, 1637–1641 (1989).

Craig et al., *J. Chem. Soc. Chem. Commun.* (1989), pp. 794–796.

Cox et al., *J. Chem. Soc. Chem. Commun.* (1989), pp. 797–798.

Paik et al., *J. Nucl. Sci.*, vol. 30, No. 10, pp. 1693–1701 (Oct. 1989).

(List continued on next page.)

*Primary Examiner*—Yogendra N. Gupta
*Attorney, Agent, or Firm*—Mathews, Woodbridge & Collins

[57] ABSTRACT

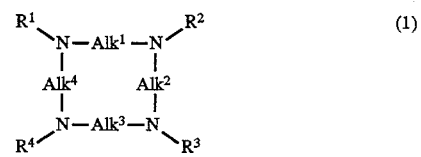

Metal complex of tetra-aza macrocycles of formula (1) wherein $Alk^1$, $Alk^2$, $Alk^3$ and $Alk^4$, which may be the same or different, is each a $C_{1-4}$alkylene chain optionally substituted by one or more optionally substituted $C_{1-6}$alkyl groups; and $R^1$, $R^2$, $R^3$ and $R^4$ which may be the same or different is each a hydrogen atom or a group $AlkR^5$ where Alk is an optionally substituted straight or branched $C_{1-6}$alkyl group and $R^5$ is a hydrogen atom or a $-CO_2H$, $-CONR^6R^7$ [where $R^6$ and $R^7$, which may be the same or different, is each a hydrogen atom or a $C_{1-6}$alkyl group] or $-P(X^1)(X^2R^8)R^9$ group where $X^1$ and $X^2$, which may be the same or different is each an oxygen or sulphur atom, $R^8$ is a hydrogen atom or an alkyl group and $R^9$ is an aliphatic, aromatic or heteroaromatic group, with the proviso that at least two of $R^1$, $R^2$, $R^3$ and $R^4$ is a group $-AlkP(X^1)(X^2R^8)R^9$ or one or $R^1$, $R^2$, $R^3$ and $R^4$ is a group $-AlkP(X^1)(X^2R^8)R^9$ and at least one of the remaining groups $R^1$, $R^2$, $R^3$ and $R^4$ is a group $-AlkCO_2H$ or $-AlkCONR^6R^7$, or a salt thereof, for use as contrast agents in nuclear magnetic resonance imaging are described.

10 Claims, 3 Drawing Sheets

OTHER PUBLICATIONS

Paik et al., *Nucl. Med. Biol.*, vol. 16, No. 5, pp. 475–481 (1989).

Deshpande et al., *Nucl. Med. Biol.*, vol. 16, No. 6, pp. 587–597 (1989).

Deshpande et al., *The Journal of Nuclear Medicine*. "Copper–67–Labeled Monoclonal Antibody Lym–1, A Potential Radio–pharmaceutical for Cancer Therapy: Labeling and Biodistribution in RAJI Tumored Mice,*"* vol. 29, No. 2, pp. 217–225 (Feb. 1988).

Mears, Claude F., "Protein Tailoring for Food and Medicine Uses edited by R.E. Feeny et al., *Attaching Metal Ions to Antibodies*", pp. 339–352 (1986).

Goodwin, D.A., et al., Abstract of "*In Complex of a New Macrocyclic Bifunctional Chelator TETA*", presented at European Nuclear Medicine Congress Meeting at Barbican, London, Sep. 3–6 (1985).

Meares et al., *Int. J. cancer Suppl.*, 2, 99–102 (1988).

Meares et al., *Br. J. Cancer*, 62, 21–26 (1990).

Gransow et al., ACS Symposium Series, No. 241, "*Generator Produced Bi–212*" (1984).

Moi et al., *Anal. Biochem.*, 148, 249–253 (1985).

Lazar et al. Inorg. Chem. 30, pp. 5016–5019, 1991.

TETRA-AZA MACROCYCLES, PROCESSES FOR THEIR PREPARATION AND THEIR USE IN MAGNETIC RESONANCE IMAGING

This application is a continuation of Ser. No. 08/175,489 filed on Dec. 29, 1993, now abandoned, which is a continuation of Ser. No. 08/041,299 filed on Mar. 29, 1993, now abandoned, which is a continuation of Ser. No. 07/793,374, filed as PCT/GB91/00605, Apr. 18, 1991 published as WO91/16081, Oct. 31, 1991, now abandoned.

FIELD OF THE INVENTION

This invention relates to tetra-aza macrocycles, to metal complexes thereof to processes for their preparation and to their use in magnetic resonance imaging.

BACKGROUND OF THE INVENTION

Proton nuclear magnetic resonance (NMR) is extensively used as a means of chemical analysis. In recent years it has also found increasing use as an imaging technique, in particular for use in examination of the human body, where it has many advantages over other imaging methods [see, for example, Andrew. E. R., Acc. Chem. Res. 16, 114–122 (1983)].

For effective NMR imaging it is usually desirable to employ a paramagnetic agent, more commonly known as a contrast agent, to enhance the sensitivity of the technique and to reduce imaging time. Numerous paramagnetic agents are available [see, for example Brasch R. C., Radiology 147, 781–788 (1983)].

A contrast agent that has recently received much attention is gadolinium, which has an unusually large magnetic moment, which efficiently relaxes magnetic nuclei. A major problem with gadolinium, however, is its toxicity to animals, and to attempt to reduce this, gadolinium has been complexed with a number of organic molecules, including diethylenetriaminepentaacetic acid (DTPA) [see for example Weinmann, H. J. et al Am. J. Roentgenology 142, 619–624, (1984)], tetraazacyclododecanetetraacetic acid (DOTA) [Bousguet, J. C., et al Radiology 166, 693–698 (1968)] and other polyamines [see for example U.S. Pat. No. 4,639,365]. Of these, Gd-DTPA is probably the best known paramagnetic contrast agent currently in clinical use, while it has recently been suggested that Gd-DOTA, with an in vitro stability five orders of magnitude greater than that of Gd-DTPA, could also be a clinically, useful contrast agent [Bousquet, J. C. et al (1988) ibid].

Despite the success of Gd-DTPA and Gd-DOTA, there are instances when they are of limited use [see for example Adzamil et al J. Med. Chem. 32, 139–144 (1989)] and there is still a general need for a contrast agent which has good enhancement of proton relaxation times, while remaining stable in vivo, and which has low toxicity at doses appropriate for contrast enhancement in a wide variety of applications. In particular, contrast agents are required which can also be used in the imaging of certain organs, such as the brain, and other tissues or lesions which are not particularly accessible to agents such as Gd-DTPA or Gd-DOTA. In such instances, large doses of Gd-DTPA or Gd-DOTA may be required to achieve satisfactory imaging, and toxicity can then begin to be a problem, with the result that the agent is no longer diagnostically useful.

There are a number of reported attempts to provide improved DOTA analogues for NMR imaging, in which a use of different ring structures and/or ring substituents has been employed [see for example European Patent Specifications Nos. 305320, 352218, 355097, 365412 and 391766, and International Patent Specifications Nos. WO89/00557 and WO89/05802].

We have now found a new class of tetra-aza macrocycles containing at least one phosphinic acid side-chain, which are capable of forming highly stable complexes with elements such as gadolinium. Compounds of the class, when complexed to gadolinium, also enhance proton relaxation times and are thus of use in NMR diagnostic techniques. The compounds have excellent metal binding properties, and advantageous solubility characteristics, and are of use in a wide variety of NMR imaging applications.

Thus according to one aspect of the invention we provide a metal complex of a compound of formula (1)

wherein $Alk^1$, $Alk^2$, $Alk^3$ and $Alk^4$, which may be the same or different, is each a $C_{1-4}$alkylene chain optionally substituted by one or more optionally substituted $C_{1-6}$alkyl groups; and $R^1$, $R^2$, $R^3$ and $R^4$ which may be the same or different is each a hydrogen atom or a group $AlkR^5$ where Alk is an additionally substituted straight or branched $C_{1-6}$alkyl group and $R^5$ is a hydrogen atom or a $-CO_2H$, $-CONR^6R^7$ [where $R^6$ and $R^7$, which may be the same or different, is each a hydrogen atom or a $C_{1-6}$alkyl group] or $-P(X^1)$ $(X^2R^8)R^9$ group where $X^1$ and $X^2$, which may be the same or different is each an oxygen or sulphur atom, $R^8$ is a hydrogen atom or an alkyl group and $R^9$ is an aliphatic, aromatic or heteroaromatic group, with the proviso that at least two of $R^1$, $R^2$, $R^3$ and $R^4$ is a group -Alk $P(X^1)(X^2R^8)$ $R^9$ or one of $R^1$, $R^2$, $R^3$ and $R^4$ is a group -Alk $P(X^1)(X^2R^8)$ $R^9$ and at least one of the remaining groups $R^1$, $R^2$, $R^3$ and $R^4$ is a group -AlkCO$_2$H or -AlkCONR$^6$R$^7$, or a salt thereof, for use as a contrast agent for nuclear magnetic resonance imaging.

It will be appreciated that formula (1) [and, where appropriate, the following formulae herein], is intended to cover all stereoisomers of the compounds concerned, including mixtures thereof.

The term "nuclear magnetic resonance" is abbreviated hereinafter to NMR.

$Alk^1$, $Alk^2$, $Alk^3$ and $Alk^4$ in the compounds of formula (1) may each be a chain $-CH_2-$, $-(CH_2)_2-$, $-(CH_2)_3-$ or $-(CH_2)_4-$, optionally substituted by one or more $C_{1-6}$alkyl, [e.g. methyl or ethyl] groups, optionally substituted by one or more groups, such as by one or more hydroxy groups. Examples of substituted $Alk^1$, $Alk^2$, $Alk^3$ and $Alk^4$ chains include $-CH_2-CH(CH_3)-$, $-CH_2-C(CH_3)_2-$ or $-CH_2-CH(CH_2OH)-$.

In the compounds for use according to the invention, alkyl groups represented by $R^6$, $R^7$ or $R^8$ may be straight or branched chain groups and may be for example $C_{1-6}$alkyl groups such methyl, ethyl, n-propyl or i-propyl groups.

The group $CONR^6R^7$ when present in compounds of formula (1) may be for example $-CONH_2$, $-CONHCH_3$, $-CON(CH_3)_2$, $-CONHCH_2CH_3$ or $-CON(CH_2CH_3)_2$.

Alk in compounds of formula (1) may be for example a methyl, ethyl, n-propyl, i-propyl, n-butyl, s-butyl or t-butyl group. Such groups may be substituted, for example, by one or more atoms or groups as described herein below. Particular substituents include for example one or more halogen atoms, e.g. fluorine or chlorine atoms, or hydroxy or phenyl groups.

Thus, particular examples of the group $AlkR^5$ include —$CH_2CO_2H$, —$CH_2CONH_2$, —$CH_2CONHCH_3$, —$CH_2CON(CH_3)_2$, —$CH_2CH(OH)CH_3$, —$CH_2CH_2CH_3$, —$CH_2CH_2CH_2$-phenyl and —$CH_2P(X^1)(X^2R^8)R^9$, especially —$CH_2P(O)(X^2H)R^9$.

When the group $R^9$ in compounds of formula (1) is an aliphatic group it may be for example an optionally substituted straight or branched chain alkyl, alkenyl, alkynyl, alkoxy or alkylthio group, optionally interrupted by one or more heteroatoms, or a cycloalkyl or cycloalkenyl group. When $R^9$ is an aromatic group it may be for example an aryl or aralkyl group. Heteroaromatic groups represented by $R^9$ include heteroaryl and heteroaralkyl groups.

Thus, for example, $R^9$ may be an optionally substituted $C_{1-10}$alkyl (e.g. $C_{1-6}$ alkyl such as methyl, ethyl, n-propyl, i-propyl, n-butyl, s-butyl or t-butyl) $C_{2-10}$alkenyl (e.g. $C_{2-6}$alkenyl such as ethene, propene, 1-butene, 2-butene, or 2-methylpropene), $C_{2-10}$alkynyl (e.g. $C_{2-6}$alkynyl such as ethyne, propyne, 1-butyne, or 2-butyne) $C_{1-10}$alkoxy (e.g. $C_{1-6}$alkoxy such as methoxy, ethoxy, n-propoxy, i-proproxy, n-butoxy, s-butoxy, or t-butoxy) or $C_{1-10}$alkylthio (e.g. $C_{1-6}$alkylthio such as methylthio, ethylthio, n-propylthio, i-propylthio, n-butylthio, s-butylthio, or t-butylthio) group optionally interrupted by one or more heteroatoms selected from —O—, —S— or —$NR^{10}$ (where $R^{10}$ is a hydrogen atom or a $C_{1-6}$alkyl group), for example an alkoxyalkyl (e.g. methoxymethyl), alkylthioalkyl (e.g. methylthiomethyl) or alkoxyalkoxy or alkylthioalkoxy (e.g. methoxymethoxy or methylthiomethoxy) group; or a $C_{3-8}$cycloalkyl (e.g. cyclopropyl, cyclobutyl, cyclopentyl, or cyclohexyl) or $C_{4-8}$cycloalkenyl (e.g. cyclobutene, cyclopentene, cyclohexene, cyclohexadiene) group.

When $R^9$ is an aryl group it may be for example an optionally substituted $C_{6-12}$aryl group such as an optionally substituted phenyl or naphthyl group.

When $R^9$ is an aralkyl group it may be for example an optionally substituted $C_{6-12}arC_{1-6}$alkyl group for example a phen$C_{1-6}$alkyl group such as benzyl or phenethyl.

When $R^9$ is a heteroaryl group it may be for example an optionally substituted $C_{4-10}$heteroaryl group containing one or more heteroatoms selected from —O—, —NH— or —S— for example a pyridyl, furanyl or thienyl group.

When $R^9$ is a heteroaralkyl group it may be for example an optionally substituted $C_{4-10}$heteroar$C_{1-6}$alkyl group containing one or more heteroatoms selected from —O—, —NH—, or —S— for example a thienyl $C_{1-6}$alkyl (e.g. thienylmethyl) or pyridyl$C_{1-6}$alkyl (e.g. pyridylmethyl) group.

Optional substituents which may be present on alkyl, alkoxy, aryl, aralkyl, heteroaryl or heteroaralkyl groups in compounds of formula (1) [for example in Alk and $R^9$, where present] include halogen atoms e.g. chlorine, bromine, fluorine or iodine atoms, or one or more groups selected from hydroxyl, $C_{1-6}$ alkyl [e.g. methyl, ethyl] trihalomethyl [e.g. trifluoromethyl], $C_{1-6}$alkoxy [e.g. methoxy or ethoxy], $C_{1-6}$alkylthio, [e.g. methylthio], hydroxy$C_{1-6}$alkyl, [e.g. hydroxymethyl or hydroxypropyl] polyhydroxy$C_{1-6}$alkyl, amino [—$NH_2$], substituted amino, [e.g. $NR^{11}R^{12}$ where $R^{11}$ is a hydrogen atom or a $C_{1-6}$alkyl group and $R^{12}$ is a $C_{1-6}$alkyl group, such as methylamino or dimethylamino], nitro, cyano, carboxyl, —$CONR^6R^7$ [e.g. —$CONH_2$], —$SO_2NR^6R^7$ [e.g. $SO_2NH_2$] aryl, [e.g. phenyl], or $C_{3-8}$cycloalkyl [e.g. cyclopropyl, cyclobutyl, cyclopentyl or cyclohexyl] groups.

Metal complexes of compounds of formula (1) include complexes wherein the metal is a transition metal with an atomic number 21 to 29, 42, 43, 44 or 75, or a lanthanide with an atomic number 57 to 70 or a Group III element with atomic number 5, 13, 31, 49 and 81 and is generally di- or tripositive and has a coordination number 6 or greater, especially 8. Examples of such metals include manganese, iron, terbium, europium, dysprosium, scandium, gadolinium, gallium and indium.

Salts of compounds of formula (1) or the metal complexes thereof include salts with inorganic or organic bases, for example alkali metal or alkaline earth metal salts such as lithium, sodium, potassium, magnesium or calcium salts; amine salts, such as those from primary, secondary or tertiary amines, for example ethanolamine, diethanolamine, morpholine, glucamine, N-methylglucamine or N,N-dimethylglucamine salts; and amino acid salts such as lysine, arginine and ornithine salts.

Particularly useful compounds of formula (1) are those wherein $Alk^1$, $Alk^2$, $Alk^3$ and $Alk^4$ is each a —$(CH_2)_2$— chain.

Another useful group of compounds of formula (1) is that wherein $R^1$, $R^2$, $R^3$ and $R^4$ is each a group -$AlkP(X^1)(X^2R^8)R^9$, particularly a group -$AlkP(O)(X_2H)R^9$, especially -$AlkP(O)(OH)R^9$. Particularly useful compounds of this type are those wherein each of $R^1$, $R^2$, $R^3$ and $R^4$ is a $CH_2P(O)(OH)R^9$ group. Another important group of compounds of this type is that wherein $R^9$ is an alkyl group, particularly a methyl group, or an optionally substituted phenyl group.

In another preference, each of the groups $R^1$, $R^2$, and $R^3$ may be for example a group -$AlkP(X^1)(X^2R^8)R^9$ and $R^4$ may be a hydrogen atom or a group -Alk, -$AlkCO_2H$ or -$AlkCONR^6R^7$. Thus for example each of the groups $R^1$, $R^2$ and $R^3$ may be a group —$CH_2P(O)(OR^8)R^9$ especially —$CH_2P(O)(OH)R^9$, e.g. where $R^9$ is an alkyl group such as methyl ethyl, n-propyl, i-propyl, n-butyl, s-butyl or t-butyl group or an aralkyl group such as a benzyl group or an optionally substituted phenyl group and $R^4$ may be a hydrogen atom or a group —$CH_2CH(OH)CH_3$, —$CH_2CO_2H$ or —$CH_2CONR^6R^7$, especially —$CH_2CONH_2$, —$CH_2CONHCH_3$ or —$CH_2CON(CH_3)_2$.

In still another preference, each of the groups $R^1$, $R^2$ and $R^3$ may be a group -$AlkP(S)(OR^8)R^9$, e.g. -$AlkP(S)(OH)R^9$ such as—$CH_2P(S)(OH)R^9$ where $R^9$ is an alkyl group such as a methyl group, or an optionally substituted phenyl group and $R^4$ may be a hydrogen atom or a group Alk, e.g. —$CH_2CH(OH)CH_3$, $AlkCO_2H$, e.g. —$CH_2CO_2H$ or $AlkCONR^6R^7$, e.g. —$CH_2CONR^6R^7$ such as —$CH_2CONH_2$, —$CH_2CONHCH_3$ or —$CH_2CON(CH_3)_2$.

One group of compounds for use according to the invention are the metal complexes of compounds of formula (1) wherein $Alk^1$, $Alk^2$, $Alk^3$, $Alk^4$, $R^1$, $R^2$, $R^3$ and $R^4$ are as defined for formula (1) with the further proviso that the group $R^9$ in at least one of the groups -$AlkP(X^1)(X^2R^8)R^9$ is as defined for formula (1) but is other than an unsubstituted alkyl or alkoxy group.

A further useful group of compounds for use according to the invention are the gadolinium complexes of the compounds of formula (1) and the salts thereof.

The following formulae (1a)–(1c) define various preferred groups of compounds for use according to the invention. It will be appreciated that the detailed definitions given above for each of the groups $R^1$–$R^5$ and Alk in respect of formula (1) also apply to these formulae.

A particularly useful group of compounds for use according to the invention are the metal complexes of the compounds of formula (1a):

(1a)

wherein $R^1$, $R^2$, and $R^3$ which may be the same or different is each a group $-AlkP(X^1)(X^2R^8)R^9$ and $R^4$ is a hydrogen atom or a group -Alk, $-AlkCO_2H$, $-AlkCONR^6R^7$ or $-AlkP(X^1)(X^2R^8)R^9$, where Alk, $X^1$, $X^2$, $R^6$, $R^7$, $R^8$ and $R^9$ are as previously defined; and the salts thereof.

In the compounds of formula (1a), the group $-AlkP(X^1)(X^2R^8)R^9$ when present is preferably a group $-AlkP(O)(OH)R^9$, especially $-CH_2P(O)(OH)R^9$, particularly where $R^9$ is an aliphatic or aryl group, such as an optionally substituted alkyl or phenyl group.

A useful group of compounds of formula (1a) has the formula (1b):

(1b)

wherein Alk is as defined for formula (1) and each $R^5$ group is a $-P(O)(X^2R^8)R^9$ group, where $X^2$, $R^8$ and $R^9$ are as previously defined; and the metal complexes and/or salts thereof.

Particularly useful compounds of formula (1b) are those wherein Alk is $-CH_2-$. Compounds of formula (1b) wherein $R^5$ is a group $-P(O)(X^2H)R^9$, especially a group $-P(O)(OH)R^9$ where $R^9$ is an aliphatic or aryl group, particularly an optionally substituted alkyl or phenyl group, such as a group $-P(O)(OH)CH_3$, or $-P(O)(OH)Ph$ [where Ph is phenyl or substituted phenyl] and the metal complexes and/or salts thereof are particularly useful. Compounds of this type where Alk is $-CH_2-$ are also important.

Gadolinium complexes of the compounds of formula (1b) are especially useful.

Particularly useful compounds for use according to the invention are the metal complexes of the compound of formula (1c):

(1c)

and the salts thereof.

The gadolinium complex of the compounds of formula (1c) and the salts thereof is a particularly useful compound.

The metal complexes of the compounds of formula (1) may be used employing conventional NMR procedures and apparatus [see for example H. J. Weinmann et al Am. J. Roentgenology ibid and U.S. Pat. Nos. 4,374,360, 4,398,148, 4,409,550, 4,425,547, 4,442,404 and 4,450,408].

Compounds of formula (1) may be employed for the preparation of contrast agents for use in NMR imaging, for example by complexation with an appropriate metal, as described herein. Thus according to another aspect of the invention we provide a compound of formula (1) or a salt thereof for use in the preparation of a contrast agent for NMR imaging.

The metal complexes of the compounds of formula (1) and the salts thereof may generally initially be formulated for use for administration to an animal, e.g. human subject using standard procedures. Thus according to a further aspect of the invention we provide a pharmaceutical composition comprising a metal complex of a compound of formula (1) or a salt together with one or more pharmaceutically acceptable carriers for use as a contrast agent for NMR imaging.

Suitable formulations include those adapted for oral or parenteral administration, e.g. by injection or infusion and may take the form of liquid preparations of metal complexes of the compounds of formula (1) and the salts thereof, such as solutions, suspensions, emulsions or syrups in oily or aqueous vehicles which may contain formulatory agents such as suspending, stabilizing and/or dispersing agents. Alternatively the metal complex may be in powder form for reconstitution with a suitable vehicle, e.g. sterile pyrogan-free water, or isotonic saline before use.

In yet another aspect of the invention, we provide the use of a metal complex of a compound of formula (1) or a salt thereof for the preparation of a pharmaceutical composition for use in NMR imaging.

Standard procedures may be used for the preparation of compositions according to the invention, depending on the formulation chosen.

The metal complexes of the compounds of formula (1) and the salts thereof may be administered at any suitable dosage, depending on the nature of the target to be imaged. Thus according to a further aspect of the invention we provide a method of enhancing NMR contrast in an animal subject which includes administering to said subject an effective amount of a metal complex of a compound of formula (1) or a salt thereof.

In general, the complexes according to the invention may be administered in amounts of 0.001 to 5 mMol/Kg.

Certain compounds of formula (1) are new and form a further aspect of the invention. Thus, according to another aspect of the invention we provide a compound of formula (2)

(2)

wherein $Alk^1$, $Alk^2$, $Alk^3$ and $Alk^4$, which may be the same or different, is each a $C_{1-4}$alkylene chain optionally substituted by one or more optionally substituted $C_{1-6}$alkyl groups; and $R^1$, $R^2$, $R^3$ and $R^4$ which may be the same or different is each a hydrogen atom or a group $AlkR^5$ where Alk is an optionally substituted straight or branched $C_{1-6}$ alkyl group and $R^5$ is a hydrogen atom or a $-CO_2H$, $-CONR^6R^7$ [where $R^6$ and $R^7$, which may be the same or different, is each a hydrogen atom or a $C_{1-6}$alkyl group] or $-P(X^1)(X^2R^8)R^9$ group where $X^1$ and $X^2$, which may be the same or different is each an oxygen or sulphur atom; $R^8$ is a hydrogen atom or an alkyl group and $R^9$ is an aliphatic, aromatic or heteroaromatic group, with the proviso that at least two of $R^1$, $R^2$, $R^3$ and $R^4$ is a group -Alk $P(X^1)(X^2R^8)$ $R^9$ or one of $R^1$, $R^2$, $R^3$ and $R^4$ is a group -Alk $P(X^1)(X^2R^8)$ $R^9$ and at least one of the remaining groups $R^1$, $R^2$, $R^3$ and $R^4$ is a group $-AlkCO_2H$ or $-AlkCONR^6R^7$, and $R^9$ in at least one of the groups $-AlkP(X^1)(X^2R^8)R^9$ is an aliphatic, aromatic or heteroaromatic group but is not an unsubstituted alkyl or alkoxy group when $R^1$, $R^2$, $R^3$ and $R^4$ are the same and the metal complexes and/or salts thereof.

A particular useful group of compounds of formula (2) has the formula (2a)

(2a)

wherein $R^1$, $R^2$, and $R^3$ which may be the same or different is each a group $AlkP(X^1)(X^2R^8)R^9$ and $R^4$ is a hydrogen atom or a group -Alk, -AlkCO$_2$H, -AlkCONR$^6$R$^7$ [where Alk, $X^1$, $X^2$, $R^6$, $R^7$, $R^8$ and $R^9$ are as defined previously] or $R^4$ is a group -AlkP(X$^1$)(X$^2$R$^8$)R$^9$ [where Alk, $X^1$, $X^2$, $R^8$, and $R^9$ are as previously defined with the proviso that $R^9$ is not an unsubstituted alkyl group] and the salts thereof.

A useful group of compounds of formula (2a) is that wherein $R^1$, $R^2$, $R^3$ and $R^4$ is each a group -AlkP(X$^1$)(X$^2$R$^8$)R$^9$ wherein $R^9$ is an aryl group. Particular compounds of this type include —CH$_2$P(O)(OH)R$^9$, where $R^9$ is an aryl group. Aryl groups represented by $R^9$ include $C_{6-12}$aryl groups such as optionally substituted phenyl or napthyl groups. Optional substituents may be those described previously and may in particular be one or more halogen atoms, e.g. chlorine, bromine fluorine or iodine atoms, $C_{1-6}$alkyl groups such as methyl groups, trihalomethyl groups, such as trifluoromethyl groups or carboxyl groups.

A further useful group of compounds of formula (2a) is that wherein $R^1$, $R^2$ and $R^3$ is each a group -AlkP(X$^1$)(X$^2$R$^8$) R$^9$ [where Alk; $X^1$, $X^2$,$R^8$ and $R^9$ are as defined in the preceding paragraph] and $R^4$ is a hydrogen atom or a group -Alk, -AlkCO$_2$H, or -AlkCONR$^6$R$^7$. In particular, $R^4$ may be a group —CH$_2$CH(OH)CH$_3$, —CH$_2$CO$_2$H, —CH$_2$CONH$_2$, —CH$_2$CONHCH$_3$, or —CH$_2$CON(CH$_3$)$_2$.

The compounds of formula (2) have excellent metal binding properties and in particular form stable complexes with metals such as gadolinium. The compounds also have good solubility characteristics and when complexed with a metal such as gadolinium are of particular use as contrast agents in NMR imaging. The suitability of such complexes for use as contrast agents may initially determined in test animals, using standard procedures, for example as described hereinafter in relation to FIG. 1.

It will be appreciated that the various preferences expressed above in relation to the compounds of formula (1) for use as contrast agents also apply to the compounds of formula (2) as just defined.

Compounds of formula (1) may be prepared by the following processes. Unless otherwise defined, the various groups Alk and Alk$^1$–Alk$^4$, $X^1$, $X^2$, and $R^1$–$R^9$ as they appear in the description below are to be understood to have the meanings described above. The following processes clearly also apply to the preparation of compounds of formula (2).

Metal complexes for use according to the invention may be prepared by reacting a compound of formula (1) or a salt thereof with a metal salt (e.g. a nitrate, halide, such as a chloride, acetate, carbonate or sulphate) or a metal oxide.

The reaction may be performed in an appropriate solvent, for example an aqueous or non-aqueous solvent (e.g. acetonitrile, acetone, propylene carbonate, dimethylformamide or dimethylsulphoxide) at any suitable temperature from 0° C. to 1000° C. such as 10° C. to 85° C.

Salts of compounds of formula (1) may be prepared by reacting a compound of formula (1) with a base in an appropriate solvent, for example an aqueous or non-aqueous solvent as described above, at any suitable temperature from 0° C. to 100° C.

Compounds of formula (1) in which one or more $R^1$, $R^2$, $R^3$ and $R^4$ is each a group AlkP(X$^1$)(X$^2$H)R$^9$ may be prepared by interconversion of a corresponding compound of formula (1) in which one or more of $R^1$, $R^2$, $R^3$ and $R^4$ is each a group AlkP(X$^1$)(X$^2$R$^8$)R$^9$ [where $R^8$ is an alkyl group] by treatment with an acid, for example an inorganic add such as hydrochloric acid at an elevated temperature, for example the reflux temperature, or by treatment with a base, for example an inorganic base such as potassium hydroxide.

Compounds of formula (1) in which $R^1$, $R^2$, $R^3$ and $R^4$ is each a group -AlkP(X$^1$)(X$^2$R$^8$)R$^9$ [where $R^8$ is an alkyl group] may be prepared by reaction of a compound of formula (2).

(3)

with a phosphine $R^9P(X^1Alk^5)(X^2R^8)$ where $R^8$ is as just defined and Alk$^5$ is an alkyl group, for example a methyl or ethyl group] in the presence of formaldehyde, paraformaldehyde or an aldehyde RCHO (where R is a $C_{1-5}$alkyl group).

The reaction may be performed in a solvent, for example an organic solvent such as an ether, e.g. a cyclic ether such as tetrahydrofuran at an elevated temperature e.g. the reflux temperature.

Where it is desired to prepare a compound of formula (1) where at least one of $R^1$, $R^2$, $R^3$ and $R^4$ is not a group AlkP(X$^1$)(X$^2$R$^6$)R$^7$, this may be achieved by initially selectively N-protecting a compound of formula (3) or a precursor thereof using an appropriate amine protecting group(s) for example a p-toluenesulphonyl group in accordance with conventional practice [see for example International Patent Specification No. WO89/01476]. The resulting N-protected compound of formula (3) may then be reacted with a reagent R$^5$AlkD (where $R^5$ is other than a —P(X$^1$)(X$^2$R$^8$)R$^9$ group and D is a displaceable group such as a halogen, e.g. chlorine, atom or a sulphonyloxy group, e.g. a methanesulphonyloxy group) in a solvent such as water or an organic solvent such as an amide e.g. dimethylformamide in the presence of a base, e.g. an inorganic base such as an alkali metal carbonate, e.g. potassium or caesium carbonate, at an elevated temperature [in this reaction, any —CO$_2$H group present in R$^5$AlkD may need to be protected, for example as an ester, e.g. a methyl ester, the acid may be regenerate after the desired reaction is complete, for example by hydrolysis using an acid such as sulphuric acid]. After reaction with R$^5$AlkD, the resulting derivatised compound of formula (3) may be deprotected using conventional procedures, and then further reacted with a phosphine $R^9P(X^1Alk^5)(X^2R^8)$ as described above to yield the desired compound of formula (1).

In a further variation, a compound of formula (3) may be reacted with a phosphine $R^9P(X^1Alk^5)(X^2R^8)$ as previously described, and the desired di- or tri-substituted product isolated, e.g. by chromatography [using e.g. alumina in a solvent such as dichloromethane]. The di- or tri-substituted product may then be reacted with a reagent R$^5$AlkD as described above to yield the desired product of formula (1).

When a compound of formula (1) is desired where one or two of $R^1$, $R^2$, $R^3$ and $R^4$ is a hydrogen atom, this may be obtained using a N-protected intermediate of formula (3) as described above, and reacting this with a phosphine R⁹P (X¹Alk⁵)(X²R⁸), followed by deprotection to yield the appropriate —N—H compound.

Intermediates of formula (3) are either known compounds or may be prepared by methods analogous to those used for the preparation of the known compounds.

Description of the Drawing

FIG. 1 illustrates the results of an imaging study performed with the complex of Example 2 in rats inoculated in the thigh region with sarcoma cells.

In the figure, A is an image of the sarcoma (arrowed) before the administration of the complex; B is an image after administration and C is a subtraction image obtained from A and B clearly showing the sarcoma.

Figure 1A:
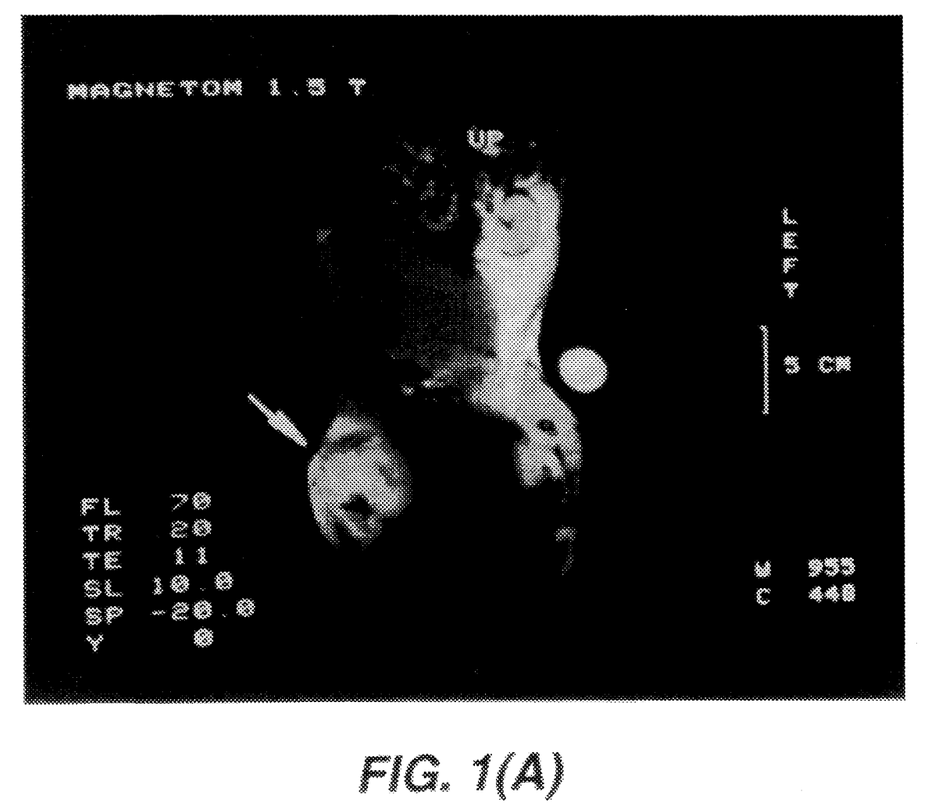
Figure 1B:
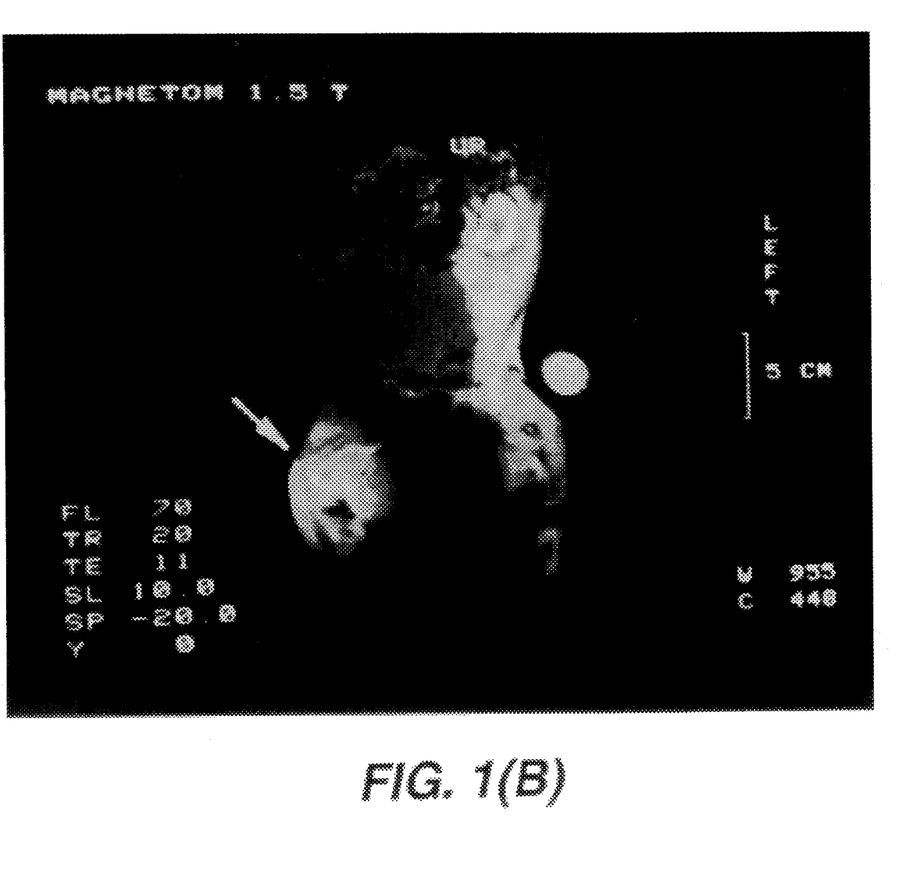
Figure 1C:
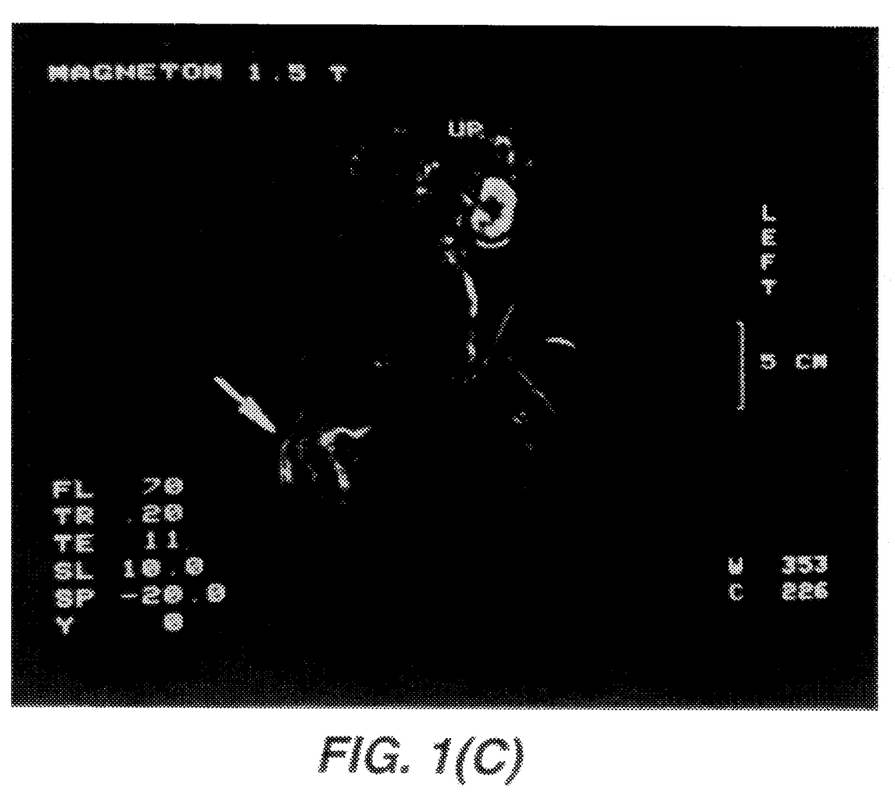

The images were obtained at 65 MHz (1.5 Tesla) using a dose of complex of 0.1 mM/Kg.

Acute Toxicity

The complexes for use in the invention are substantially non-toxic at imaging doses. Thus for example the complex of Example 2 caused no deaths when intravenously administered to mice at single doses up to 12 mM/Kg body weight.

The following Examples illustrate the preparation of compounds for use according to the invention.

EXAMPLE 1

Preparation of the compound of formula 1(c) and the corresponding tetra ethyl ester.

(a) To a solution of 1,4,7,10-tetrazacyclododecane (0.5 g) in dry tetrahydrofuran (30 ml) was added diethoxymethylphosphine (2.37 g) and paraformaldehyde (1.13 g) and the mixture was heated to reflux with azeotropic removal of water (Soxhlet, 3A sieves). After 18 h solvent was removed under reduced pressure and the residue was purified by chromatography on alumina (0 2% $CH_3OH$ in $CH_2Cl_2$) to yield a pale yellow oil (948 mg) Rf 0.5 (5% MeOH/ $CH_2Cl:Al_2O_3$). δp ($CDCl_3$) 51.6, 51.8, 51.9, (diastereoisomers) δc ($CDCl_3$) 13.44 (d, $J_{CP}$ 91 Hz, $PCH_3$), 16:42 ($CH_3$), 54.18 ($CH_2N$ ring), 54.30 (d, $J_{CP}$ 110 Hz, $CH_2P$), 59.82 ($CH_2O$). $δ_H$($CDCl_3$). 1.31 (12H, t, $CH_3CH_2$) ,1.57 (12H, d, J=13.7 Hz, $CH_3P$), 2.64–3.07 (24H, mult., $CH_2N$), 4.07 (8H, dq, $CH_2O$). m/e (d.c.i.) 652($M^+$), 533 ($M^+PC_3H_8O_2$).

(b) The tetraester prepared in Part (a) (115 mg) in hydrochloric acid (6M, 20 ml) was heated to reflux (100° C.) for 36 h. After removal of solvent and drying under vacuum (40° C., 0.01 mmHg) the compound of formula 1(b) was obtained as a glassy foam. δ($D_2O$) 41.03. δc($D_2O$) 14.86 (d, $J_{CP}$ 94 Hz, $CH_3P$), 50.70 ($CH_2N$), 51.64 (d, $J_{CP}$ 118.3 Hz, $CH_2$) δH($D_2O$) 1.41 (12H, d, J=14.1 Hz, $CH_3P$), 3.37 (24H, Br, $CH_2N$) m/e (negative FAB, glycerol) 540⁺ ($M^+$), 539 ($M^+$–1), 538 (M+–2).

EXAMPLE 2

Preparation of the Gadolinium Complex of the Compound of Formula (1c)

To a solution of the tetraphosphinic acid prepared in Example 1(b) (400 mg) in MilliQ water (10 ml) was added gadolinium oxide (133 mg) and the suspension was heated at 70° C. for 2 h. After removal of solvent the gadolinium complex of the compound of formula 1(b) was obtained as a colourless glass m/e (negative FAB, glycerol) 696, 694, 693, 692, 691.

EXAMPLE 3

Reaction scheme for the synthesis of Compound (D)

Synthesis of (A)

1,4,7,10-Tetra-azacyclododecane (1 g, 5.8 mmol) was stirred in dry tetrahydrofuran (50 cm³) under an argon atmosphere. To this was added paraformaldehyde (0.6 g) and methyldiethoxyphosphine (2.6 g). The mixture was heated under reflux over molecular sieves for about 18 hrs to give a cloudy solution. The solution was filtered and the solvent was evaporated under vacuum. The product was purified by column chromatography using alumina with a gradient from dichloromethane to 4% methanol-dichloromethane as eluent ($R_f$ product=0.28 5% methanoldichloromethane), $^1$HNMR ($\delta$CDCl$_3$); 9H (t, O—CH$_2$—C$\underline{H}_3$) 1.4 ppm, 9H (d, P—C $\underline{H}_3$) 1.53 ppm, 22H (broad, m, C$\underline{H}_2$—C$\underline{H}_2$ and N—C$\underline{H}_2$) centered at 2.8 ppm, 6H (m, O—C$\underline{H}_2$) centered at 4.1 ppm, m/z 533 (100, M$^+$+1), 425 (89, M$^+$—P(O)(OC$_2$H$_5$)(CH$_3$)).

Synthesis of (B)

Methyl amine hydrochloride (13.5 g) was added to a stirring solution of 1,2-dichloroethane (150 cm$^3$) and sodium hydroxide (16 g in 25 cm$^3$ of water). The mixture was cooled to −10° C. using an ice/salt/ethanol bath. Bromoacetyl bromide (31.5 g) in 1,2-dichloromethane (25 cm$^3$) was added to the solution with a rate to keep the temperature of the solution below −10° C. After the addition, the mixture was warmed to room temperature, the organic layer was separated, dried with magnesium sulphate and the solvent was evaporated under vacuum to give a pale brown solid. The product was isolated as white crystals by sublimation (25° C., 0.05 mmHg). $^1$HNMR ($\delta$, CDCl$_3$); 3H (d, H—N—C$\underline{H}_3$) 2.87 ppm, 2H (s, Br—C$\underline{H}_2$) 3.9 ppm, 1H (broad, s, $\underline{H}$—N)6.6 ppm.

Synthesis of (C)

The compound (A) (0.1 g) and potassium carbonate (0.03 g, 1.8×10$^{-4}$ mol) were stirred in anhydrous dimethyl formamide (5 cm$^3$) under an argon atmosphere. To this was added compound B (0.03 g, 1.8×10$^{-4}$ mol) and the mixture was heated at 80° C. for about 16 hrs to give a cloudy solution. The solvent was evaporated and the residual mass was redissolved in dichloromethane was filtered to give a clear solution. The solvent was evaporated and the crude product was purified by column chromatography using alumina with a gradient from dichloromethane to 2% methanol-dichloromethane as eluent ($R_f$ product=0.6, 10% methanol-dichloromethane). $^1$HMNR ($\delta$, CDCl$_3$); 9H (t, CH$_2$—C$\underline{H}_3$) 1.31 ppm, 9H (d, P—C$\underline{H}_3$) 1.5 ppm, 27H (broad, m, C$\underline{H}_2$—C$\underline{H}_2$ and N—C$\underline{H}_2$ and N—C$\underline{H}_3$) centered at 2.85 ppm, 6H (q, P—O—C$\underline{H}_2$) 4.06 ppm, 1H (broad, s, N—$\underline{H}$) 8.2 ppm, m/z 604 (100, M$^+$+1), 12.5, M$^+$—CH$_2$C(O)NHMe).

Synthesis of (D)

The compound C (0.05 g, 5.9×10$^{-4}$ mol) was treated with KOH/H$_2$O and the $^1$HNMR spectrum of the reaction mixture comprised resonances corresponds to ethanol and the hydrolysed product D, $^1$HNMR ($\delta$D$_2$O); 9H (d, P—C$\underline{H}_3$) 1.2 ppm, 27H (broad, m, C$\underline{H}_2$—C$\underline{H}_2$, N—C$\underline{H}_2$ and N—C$\underline{H}_3$) centered at 2.66 ppm,

Compounds of formula (1) in which R$^1$, R$^2$ and R$^3$ is each —CH$_2$P(O)((OH)CH$_3$ and R$^4$ is —CH$_2$CH(OH)CH$_3$ or —CH$_2$CH$_2$CH$_2$OH were prepared in similar fashion to compound (D) from compound (A) except that propylene oxide or ethylene oxide was used in place of compound (B).

EXAMPLE 4

Reaction Scheme for the Synthesis of Compound (F).

-continued
Reaction Scheme for the Synthesis of Compound (F).

Synthesis of (E)

1,4,7,10-Tetra-azacyclododecane (0.5 g) was stirred in dry Tetrahydrofuran (30 cm$^3$) under an argon atmosphere. To this was added paraformaldehyde (0.5 g) and phenyldimethoxyphosphine (2.5 g) and the mixture was heated under reflux over molecular sieves for about 16 hrs to give a yellow cloudy solution. The solution was filtered and the solvent was evaporated under vacuum. The crude product was purified by column chromatography using alumina with a gradient from dichloromethane to 2% methanol-dichloromethane ($R_f$ product=0.63 10% methanol-dichloromethane). $^1$HNMR ($\delta$CDCl$_3$); 16H (broad, m, C$\underline{H}_2$—C$\underline{H}_2$) centered at 2.42 ppm, 8H (broad, d, N—C$\underline{H}_2$—P) at 2.9 ppm, 12H (d, P—O—C$\underline{H}_3$) 3.55 ppm. 12H (m, Ph) 7.4 ppm, 8H (m, Ph) 7.75 ppm, M/z 845 (100, M$^+$+1).

Synthesis of (F)

The compound (E) (0.05 g) was heated at 110° C. with hydrochloric acid (6M) for 16 hrs and the solvent was evaporated to dryness in vacuo. $^1$HNMR ($\delta$, D$_2$O); 24H (broad, m) centered at 3.5 ppm, 20H (broad, m) centered at 24 ppm, $^{31}$P—($^1$H)NMR; (broad) 21.5 ppm, pD=0.45

EXAMPLE 4

Intermediate 1

Preparation of HOCH$_2$P(O)(OH)(CH$_2$)$_3$NHCOPh

To a solution of N-benzamido allylamine (7.47 g) and hypophosphorus acid (8.66 g, 50% solution) in dioxane (100 ml) was added t-butlperoxide (0.4 g) and the mixture was heated to reflux for 18 h. Solvents were removed under reduced pressure and $^1$HNMR analysis of the residue revealed that the olefinic resonances had disappeared. The residue was redissolved in dioxane (50 ml) and paraformaldehyde (25 g) was added and the mixture heated to reflux for 72 h. After removal of solvent the residue was chromatographed on silica (eluant 70% CH$_2$Cl$_2$, 25% methanol, 5% NH$_4$OH) to yield the ammonium salt of the title acid as pale yellow glass: $\delta$p (D$_2$O)+41.1 ppm; $\delta$c (D$_2$O) 170.04 (CONH), 134.0 (C$_5$H$_5$$\underline{C}$CO); 132.28, 128.98, 127.22 (CH), 59.73 (PCH₂OH, d, J$_{CP}$ 99 Hz); 41.01 (CONHCH₂); 25.12 (PCH₂CH₂, d, J$_{CP}$=81 Hz); 22.03 (PCH₂CH₂CH₂NHCO) δ$_H$ (D₂O) 7.79 (2H, dd, ortho ArH), 7.57 (4H mult, NHCO+ AZrH); 3.81 (2H, d, J=6 Hz, PCH₂OH); 3.71 (2H, t, J=6.9 Hz, CH₂NCO), 1.8 (4H, mult, PCH₂CH₂).

Intermediate 2

Preparation of HOCH₂P(O)(OEt)(CH₂)₃NHCOPh

To intermediate 1 (5 g) in distilled water (50 ml) was added Dowex strong acid ion exchange resin (30 g, H⁺ form) and after filtration the filtrate was evaporated under reduced pressure and the residue treated with triethylorthoformate (25 ml) and the mixture heated under argon at 90° C. for 96 h. After removal of HC(OEt)₃ under reduced pressure the residue was chromatographed on silica (CH₂Cl₂=5 to 10% methanol gradient) to yield a mixture of the desired alcohol ester and the mixed orthoformate ester. Treatment of this mixture with ethanol (50 ml, 1 ml, concentrated HCl) followed heating to reflux (36 h), evaporation and subsequent chromatographic purification as before yielded the title alcohol ester as a pale yellow oil, (4 g). m/e (d.c.i.) 286 (M⁺+1). δp (CDCl₃) 53.7 ppm δ$_H$ (CDCl₃) 7.71 (2H, dd, ortho, CH), 7.25 (3H, mult, atom CH), 6.85 (1H, brt, NHCO), 4.05 (1H, brs OH), 3.81 (2H, dq, CH₂O), 3.70 (1H, br, d, CH₂OH); 3.31 (2H, t, HNCH₂), 1.75 (4H, mult., PCH₂CH₂); 1.05 (3H, t, CH₃). δ$_c$ (CDCl₃/CD₃CO₂D) 168.56 (CONH) 132.98 (C₅H₅CO); 131.11, 127.82, 126.58 (CH); 56.16 (PCH₂OH, d, J$_{CP}$=90 Hz); 20.33 (CH₂); 15.37 (CH₃).

Intermediate 3

Preparation of MsOCH₂P(O)(OEt)(CH₂)₃NHCOPh

To a suspension of Intermediate 2 (0.57 g) in dry tetrahydrofuran (50 ml) at 0° C. was added triethylamine (1 g) and methanesulphonyl chloride (1.14 g) under argon). After 2 h stirring, ethanol (5 ml) was added and the mixture stirred for 20 min at 0° C., solvent removed under reduced pressure, and the residue taken up in ethyl acetate (30 ml), filtered and evaporated to give a residue which was chromatographed on silica gel (eluant 2 to 5% methanol in CH₂Cl₂) to yield the title mesylate as a colourless oil (390 mg) m/e (δ.c.i, CH₂Cl₂) 364 (M⁺+1). δp (CDCl₃) 45.96 ppm, δ$_c$ (CDCl₃) 168.6 (NHCO); 134.0 (CH₅H₅CCO); 131.4, 128.4, 129.3 (CH); 62.2 (POCH₂), 61.2 (PCH₂OMs, d, J$_{PC}$=70 Hz); 39.62 (CONHCH₂), 37.6 (OSO₂CH₃); 24.0 (PCH₂CH₂, d, J$_{PC}$=100 Hz); 21.2 (CH₂), 15.4 (CH₃)

(a) Preparation of a Compound of Formula (1) where R¹) is —CH₂P(O)(OEt)(CH₂)₃NHCOPh and R², R³ and R⁴ is each —H To a solution of 1,4,7,10-tetrazacyclododecane (0.16 g) in dry dimethylformamide (25 ml) was added potassium carbonate (0.13 g) at 60° C. and a solution of Intermediate 3 (0.167 g) in dimethylformamide (15 ml) over a period of 2 h under N₂. After 64 h, hplc analysis (CM300) revealed that reaction was not progressing and solvent was removed under reduced pressure. The crude residue was redissolved in dichloromethane (30 ml), filtered and evaporated before purification on a CM-300 column to yield the title monoalkylated amine (0.05 g) as a pale yellow oil. R$_t$=8.2 min (CM300 hplc). δ$_H$ (CDCl₃) 1.30 (3H, t, J=76 Hz, OCH₂CH₃), 1.97 (5H, mult, CH₂CH₂N+NH), 2.64–2.94 (20H, mult, CH₂P), 3.55 (2H, dt, CONHCH₂) 4.06 (2H, dq, OCH₂), 7.38–7.47 (3H, mult, aryl CH), 7.93 (2H, dd, orthoCH), 8.55 (1H, t, CONH). m/e (c.i.) 440 (M⁺+1) 394 (M⁺—OC₂H₅)

(b) Preparation of a Compound of Formula (1) where R-¹ is —CH₂P(O)(OEt)(CH₂)₃NHCOPh and R², R³ and R⁴ is each —CH₂P(O)(OEt)CH₃

To a solution of the Compound of Example 1 (0.015 g) in dry dimethylformamide (1 ml) was added potassium carbonate (16 mg) and MsOCH₂P(OEt)₂CH₃ (25 mg) under N₂. After heating to 80° C. for 16 h, t.l.c. (Al₂O₃) and hplc analysis (CM300) indicated no further reaction had occurred. After removal of solvent under reduced pressure, the residue was treated with dichloromethane (10 ml) filtered and evaporated to yield a residue which was purified by chromatography on alumina (eluant 0 to 2% methanol in CH₂Cl₂) to give the title tetraester as a colourless oil (11 mg), R$_t$ (CM300, hplc) 4.6 min. δ$_H$ (CDCl₃) 1.30 (12H, t, J=7.2, CH₃CH₂), 1.49 (9H, d+d+d, PCH₃), 1.80–3.70 (30H, mult., br., CH₂N+CH₂P+CH₂C) 4.05 (8H, dq, OCH₂), 7.39 (3H, mult, arylCH), 7.92 (2H, dd, ortho CH), 8.35 (1H, br, NHCO). m/e (c.i.) 800 (M⁺+1).

(c) Preparation of a Compound of Formula (1) where R¹ is —CH₂P(O)(OH)(CH₂)₃NH₂and R², R³ and R⁴ is each —CH₂P(O)(OH)CH₃

Hydrolysis of the tetraester of Part (b) (6M hydrochloric acid, 110° C., 48 h) afforded after removal of solvent the title amino-tetraacid δ$_H$ (CDCl₃) 1.35 (9H, d), 1.55–1.85 (4H, m), 2.6–3.7 (30H, m), 7.35 (2H, d), 8.35 (2H, d).

We claim:

1. A metal complex of a compound of the formula:

wherein:

each of R¹, R², R³, and R⁴, independently of the other is hydrogen or —CH₂—R⁵;

R⁵ is hydrogen, in which each of R⁶ and R⁷ independently of the other is hydrogen or alkyl of 1 to 6 carbon atoms; and

R⁹ is phenyl or benzyl, unsubstituted or substituted with one or more members selected from the group consisting of halo, hydroxy, trifluoromethyl, nitro, cyano, carboxy, phenyl, alkyl of 1 to 6 carbon atoms, alkoxy of 1 to 6 carbon atoms, alkylthio of 1 to 6 carbon atoms, hydroxyalkyl of 1 to 6 carbon atoms, polyhydroxyalkyl of 2 to 6 carbon atoms, cycloalkyl of 3 to 6 carbon atoms, —CONR⁶R⁷, —SONR⁶R⁷, amino, and —NR¹¹R¹² in which R⁶ and R⁷ are as defined above, R¹¹ is hydrogen or alkyl of 1 to 6 carbon atoms, and R¹² is alkyl of 1 to 6 carbon atoms; provided either that (i) at least two of R¹, R², R³ and R⁴ is a group —CH₂—P(=O)(—OH)R⁹ or (ii) one of R¹, R², R³ and R⁴ is a group —CH₂—P(=O)(—OH)R⁹ and at least one of the remaining groups R¹, R², R³ and R⁴ is a group —CH₂—CO₂H or —CH₂ —CONR⁶R⁷;

or a salt thereof.

2. A metal complex according to claim 1 wherein each of R¹, R², R³, and R⁴ is

3. A metal complex according to claim 1 wherein each of $R^1$, $R^2$, and $R^3$ is and $R^4$ is hydrogen,

4. A metal complex according to claim 1 wherein $R^9$ is benzyl.

5. A metal complex according to claim 1 wherein the metal is gadolinium.

6. In the method of nuclear magnetic resonance imaging, the improvement which comprises employing as the contrast agent a metal complex of a compound of the formula:

wherein:

each of $R^1$, $R^2$, $R^3$, and $R^4$, independently of the other is hydrogen or —CH$_2$—R$^5$;

$R^5$ is hydrogen, in which each of $R^6$ and $R^7$ independently of the other is hydrogen or alkyl of 1 to 6 carbon atoms; and $R^9$ is phenyl or benzyl unsubstituted or substituted with one or more members selected from the group consisting of halo, hydroxy, trifluoromethyl, nitro, cyano, carboxy, phenyl, alkyl of 1 to 6 carbon atoms, alkoxy of 1 to 6 carbon atoms, alkylthio of 1 to 6 carbon atoms, hydroxyalkyl of 1 to 6 carbon atoms, polyhydroxyalkyl of 2 to 6 carbon atoms, cycloalkyl of 3 to 6 carbon atoms, —CONR$^6$R$^7$, —SONR$^6$R$^7$, amino, and —NR$^{11}$R$^{12}$ in which R$^6$ and R$^7$ are as defined above, R$^{11}$ is hydrogen or alkyl of 1 to 6 carbon atoms, and R$^{12}$ is alkyl of 1 to 6 carbon atoms;

provided either that (i) at least two of $R^1$, $R^2$, $R^3$ and $R^4$ is a group —CH$_2$—P(=O)(—OH)R$^9$ or (ii) one of $R^1$, $R^2$, $R^3$ and $R^4$ is a group —CH$_2$—P(=O)(—OH)R$^9$ and at least one of the remaining groups $R^1$, $R^2$, $R^3$ and $R^4$ is a group —CH$_2$—CO$_2$H or —CH$_2$ —CONR$^6$R$^7$;

or a salt thereof.

7. The method according to claim 6 wherein the metal of said complex is gadolinium.

8. The method according to claim 6 wherein each of $R^1$, $R^2$, $R^3$, and $R^4$ is

9. The method according to claim 6 wherein $R^9$ is benzyl.

10. The method according to claim 6 wherein each of $R^1$, $R^2$, and $R^3$ is and $R^4$ is hydrogen,

* * * * *